United States Patent
Belbruno et al.

(12) 
(10) Patent No.: US 11,156,622 B2
(45) Date of Patent: Oct. 26, 2021

(54) MOLECULARLY-IMPRINTED-POLYMER COATED CONDUCTIVE NANOPARTICLES FOR COTININE DETECTION, AND ASSOCIATED DEVICES AND METHODS

(71) Applicant: THE TRUSTEES OF DARTMOUTH COLLEGE, Hanover, NH (US)

(72) Inventors: Joseph J. Belbruno, Hanover, NH (US); Ziyi Chai, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 312 days.

(21) Appl. No.: 16/091,568

(22) PCT Filed: Apr. 5, 2017

(86) PCT No.: PCT/US2017/026056
§ 371 (c)(1),
(2) Date: Oct. 5, 2018

(87) PCT Pub. No.: WO2017/176830
PCT Pub. Date: Oct. 12, 2017

(65) Prior Publication Data
US 2019/0120863 A1 Apr. 25, 2019

Related U.S. Application Data

(60) Provisional application No. 62/318,700, filed on Apr. 5, 2016.

(51) Int. Cl.
*G01N 33/94* (2006.01)
*G01N 27/12* (2006.01)
(Continued)

(52) U.S. Cl.
CPC .......... *G01N 33/94* (2013.01); *G01N 27/127* (2013.01); *G01N 33/493* (2013.01); *B82Y 15/00* (2013.01); *G01N 2600/00* (2013.01)

(58) Field of Classification Search
CPC .... G01N 33/94; G01N 33/493; G01N 27/127; G01N 2600/00; B82Y 15/00
See application file for complete search history.

(56) References Cited

U.S. PATENT DOCUMENTS

2007/0128069 A1 6/2007 Louis et al.
2009/0152537 A1 6/2009 Kim et al.
(Continued)

FOREIGN PATENT DOCUMENTS

CN 104655695 A 5/2015

OTHER PUBLICATIONS

Uzun, Lokman, and Anthony PF Turner. "Molecularly-imprinted polymer sensors: Realising their potential." Biosensors and Bioelectronics 76 (2015): 131-144. (Year: 2015).*
(Continued)

*Primary Examiner* — Robert J Eom
(74) *Attorney, Agent, or Firm* — Lathrop GPM LLP

(57) ABSTRACT

A device for detecting cotinine includes (a) a film that includes a plurality of molecularly-imprinted-polymer (MIP) coated conductive nanoparticles having specific affinity for binding with cotinine, and (b) two electrodes in contact with the film for passing electrical current through the film to detect binding with cotinine as a change in electrical conductivity of the film. A MIP coated conductive nanoparticle for detecting cotinine includes (a) a conductive nanoparticle, (b) a silicon dioxide coating formed on the conductive nanoparticle and forming a first shell around the conductive nanoparticle, and (c) an MIP coating formed on the silicon dioxide coating and forming the second shell, wherein the MIP coating includes a polymer molecularly imprinted with cotinine to provide specific affinity for binding of cotinine to the MIP coated conductive nanoparticle
(Continued)

such that the cotinine is detectable as a change in electrical conductivity of the MIP coated conductive nanoparticle.

16 Claims, 9 Drawing Sheets

(51) Int. Cl.
  G01N 33/493 (2006.01)
  B82Y 15/00 (2011.01)

(56) References Cited

U.S. PATENT DOCUMENTS

2010/0039124 A1  2/2010  Belbruno et al.
2013/0153420 A1  6/2013  Hu
2015/0079697 A1*  3/2015  Belbruno ............ G01N 27/126
                                                        436/501

OTHER PUBLICATIONS

Franqui, Lidiane Silva, et al. "Synthesis and characterization of a magnetic molecularly imprinted polymer for the selective extraction of nicotine and cotinine from urine samples followed by GC-MS analysis." Analytical Methods 7.21 (2015): 9237-9244. (Year: 2015).*
Li, Shuhuai, et al. "Synergetic dual recognition and separation of the fungicide carbendazim by using magnetic nanoparticles carrying a molecularly imprinted polymer and immobilized β-cyclodextrin." Microchimica Acta 183.4 (2016): 1433-1439. (Year: 2016).*
Whitcombe, Michael J., et al. "The rational development of molecularly imprinted polymer-based sensors for protein detection." Chemical Society Reviews 40.3 (2011): 1547-1571. (Year: 2011).*
PCT/US2017/026056 International Search Report and Written Opinion dated Aug. 25, 2017, 13 pp.
Antwi-Boampong et al. (2014) "A selective molecularly imprinted polymer-carbon nanotube sensor for cotinine sensing." Journal of Molecular Recognition, Jan. 1, 2014, vol. 27. No. 1, pp. 37-38.
Chen et al. (2015) "Preparation and Characterization of Nonylphenol Magnetic Molecularly Imprinted Polymer." Journal of the Chemical Society of Pakistan, Dec. 31, 2015, vol. 37. No. 6, pp. 1144-1145, 1147.

* cited by examiner

MOLECULARLY-IMPRINTED-POLYMER COATED CONDUCTIVE NANOPARTICLES FOR COTININE DETECTION, AND ASSOCIATED DEVICES AND METHODS

CROSS-REFERENCE TO RELATED APPLICATIONS

The present application is a 35 U.S.C. § 371 filing of International Application No. PCT/US2017/026056, filed Apr. 5, 2017, which claims the benefit of priority from U.S. Provisional Application Ser. No. 62/318,700 filed Apr. 5, 2016, which is incorporated herein by reference in its entirety.

BACKGROUND

Cotinine is the predominant metabolite of nicotine. While nicotine is present in a subject only for a couple of hours after exposure to cigarette smoke, cotinine is present in a subject for several days after exposure to cigarette smoke. Thus, the level of cotinine in the blood, urine, or saliva of a subject is an indication of the subject's exposure to cigarette smoke over a period of several days leading up to the test. Cotinine testing is most commonly used in smoking cessation programs to monitor compliance. However, cotinine testing is also used in other situations such as in employee wellness programs and for monitoring required in cases of court-mandated no-smoking directives. The most widely used commercially available cotinine tests are based on urine testing. In these tests, sufficient concentration of cotinine in a urine sample results in a color change of a test strip. A human operator or user reads this color change by visual inspection. A positive test result occurs only at concentrations associated with first-hand cigarette smoking.

SUMMARY

In an embodiment, a molecularly-imprinted-polymer (MIP) coated conductive nanoparticle for detecting cotinine includes (a) a conductive nanoparticle capable of conducting an electrical current, (b) a silicon dioxide coating formed on the conductive nanoparticle and forming a first shell around the conductive nanoparticle, and (c) an MIP coating formed on the silicon dioxide coating and forming the second shell. The MIP coating includes a polymer molecularly imprinted with cotinine to provide specific affinity for binding of cotinine to the MIP coated conductive nanoparticle such that the cotinine is detectable as a change in electrical conductivity of the MIP coated conductive nanoparticle.

In an embodiment, a device for detecting cotinine includes (a) a film including a plurality of MIP coated conductive nanoparticles having specific affinity for binding with cotinine, and (b) two electrodes in contact with the film for passing electrical current through the film to detect binding with cotinine as a change in electrical conductivity of the film.

In an embodiment, a method for detecting cotinine in a liquid sample includes exposing a film to the liquid sample. The film includes MIP coated conductive nanoparticles having specific affinity for binding with cotinine, and the film has electrical conductivity sensitive to binding with cotinine. The method further includes measuring electrical conductivity of the film, and determining the presence of cotinine in the liquid sample based upon the electrical conductivity.

In an embodiment, a method for manufacturing a device for detecting cotinine includes (a) making a solution including a polymer, a solvent, and cotinine, and (b) adding silicon dioxide coated conductive nanoparticles to the solution to form a shell, including the polymer and the cotinine, around each of the silicon dioxide coated metal nanoparticles through binding of the polymer to the silicon dioxide, so as to form polymer-silicon dioxide coated conductive nanoparticles. The method further includes extracting the polymer-silicon dioxide coated conductive nanoparticles from the solution, and removing the cotinine from the polymer-silicon dioxide coated conductive nanoparticles to form molecularly-imprinted-polymer (MIP) coated conductive nanoparticles having (i) specific affinity for binding with cotinine and (ii) electrical conductivity sensitive to said binding with cotinine.

DETAILED DESCRIPTION OF THE EMBODIMENTS

Figure 1:
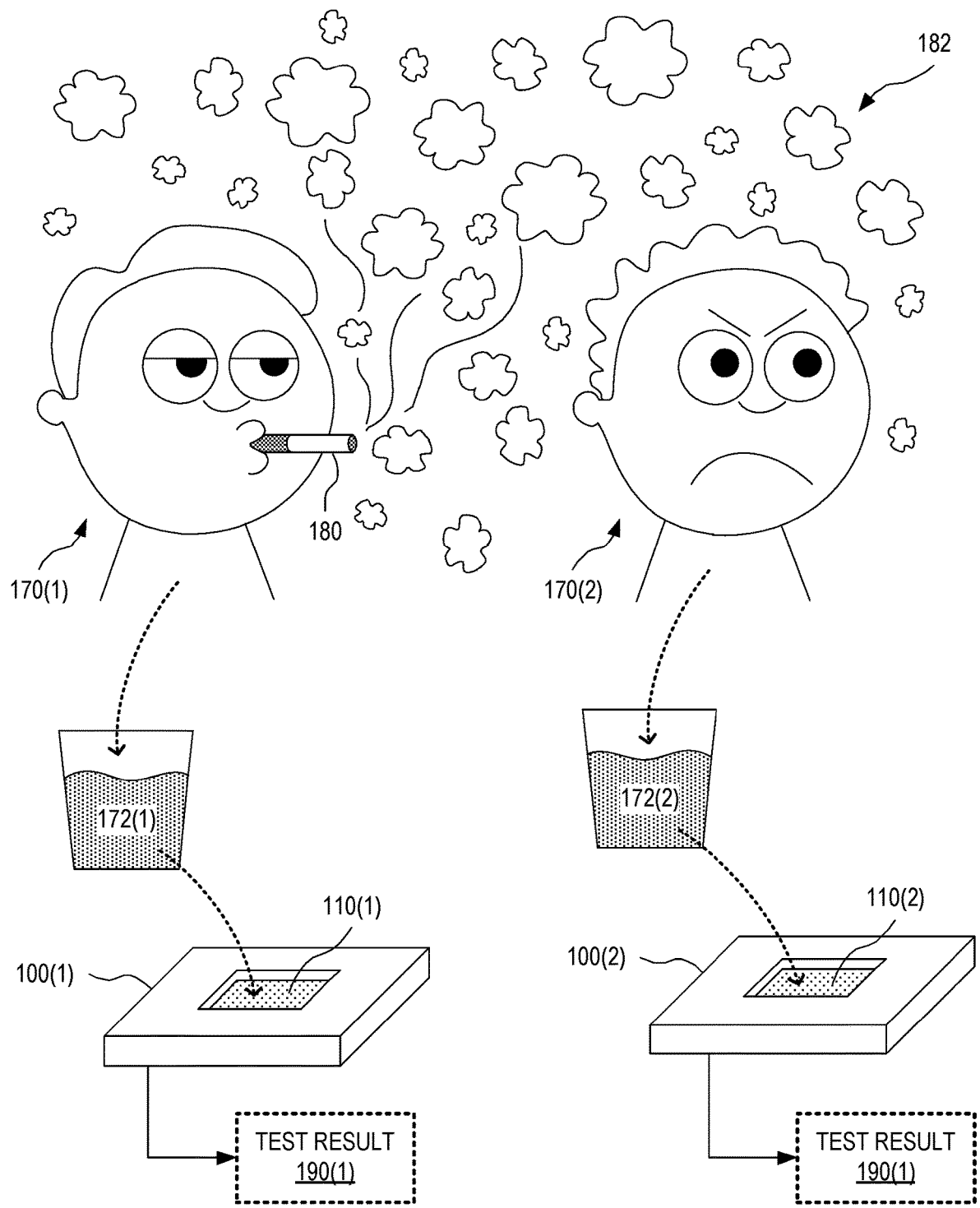
FIG. 1 illustrates a device for detecting cotinine in a liquid sample, according to an embodiment.

FIG. 1 illustrates one exemplary device 100 for detecting cotinine in a liquid sample 172. Liquid sample 172 is, for example, a urine sample of a subject 170. In FIG. 1 shows two instances 100(1) and 100(2) of device 100, two corresponding instances 172(1) and 172(2) of liquid sample 172, and two corresponding instances 170(1) and 170(2) of subject 170. In the exemplary scenarios shown in FIG. 1, subject 170(1) is a first-hand cigarette smoker smoking a cigarette 180, while subject 170(2) is exposed only to second-hand cigarette smoke 182. Device 100 includes molecularly-imprinted-polymer (MIP) coated conductive nanoparticles 110 to detect the presence of cotinine in liquid sample 172 when placed in or on device 100. MIP coated conductive nanoparticles 110 are discussed in further detail below in reference to FIGS. 4 and 5. MIP coated conductive nanoparticles 110 of devices 100(1) and 100(2) are labeled 110(1) and 110(2), respectively. MIP coated conductive nanoparticles 110 have (a) specific affinity for binding with cotinine and (b) electrical conductivity sensitive to the amount of cotinine bound thereto. A measurement of the electrical conductivity of MIP coated conductive nanoparticles 110 produces a test result 190. FIG. 1 shows two instances 190(1) and 190(2) of test results 190, respectively produced by devices 100(1) and 100(2).

Test result 190 indicates the presence of a detectable amount of cotinine in liquid sample 172. Test results 190 may further indicate the detected concentration of cotinine in liquid sample 172. Readout of device 100 is performed electronically and does not require a subjective evaluation of device 100. This is in contrast to the conventional color-change based cotinine tests available on the commercial market, which suffer from human subjectivity in the visual readout process. Device 100 eliminates the subjectivity of a human readout and is at least for this reason more reliable than the conventional tests.

In addition, at least in part by virtue of MIP coated conductive nanoparticles 110, device 100 is more sensitive than the conventional tests and is capable of detecting cotinine in liquid sample 172 at low concentrations associated only with second-hand smoking, such as experienced by subject 170(2). Furthermore, in certain embodiments, test result 190 indicates the concentration of cotinine in liquid sample 172, either as a relative measure or an absolute measure, such that device 100 is capable of distinguishing between first-hand smoking, such as by subject 170(1), and second-hand smoking, such as by subject 170(2). Such embodiments of device 100 may further be capable of indicating the amount of first-hand smoking and/or the severity of second-hand smoking. In an embodiment, device 100 is calibrated such that test result 190 indicates the cotinine concentration of liquid sample 172 in absolute terms, for example in units of nanograms per milliliter (ng/ml). Alternatively, test result 190 may indicate the cotinine concentration of liquid sample 172 in relative terms.

In one embodiment, device 100 is configured for single-use and is discarded after testing of a single liquid sample 172. In another embodiment, device 100 is configured for repeated use. In this embodiment, device 100 is washed after testing of each liquid sample 172 to remove cotinine bound to MIP coated conductive nanoparticles 110 of device 100 for unbiased testing of the next liquid sample 172.

Figure 2:
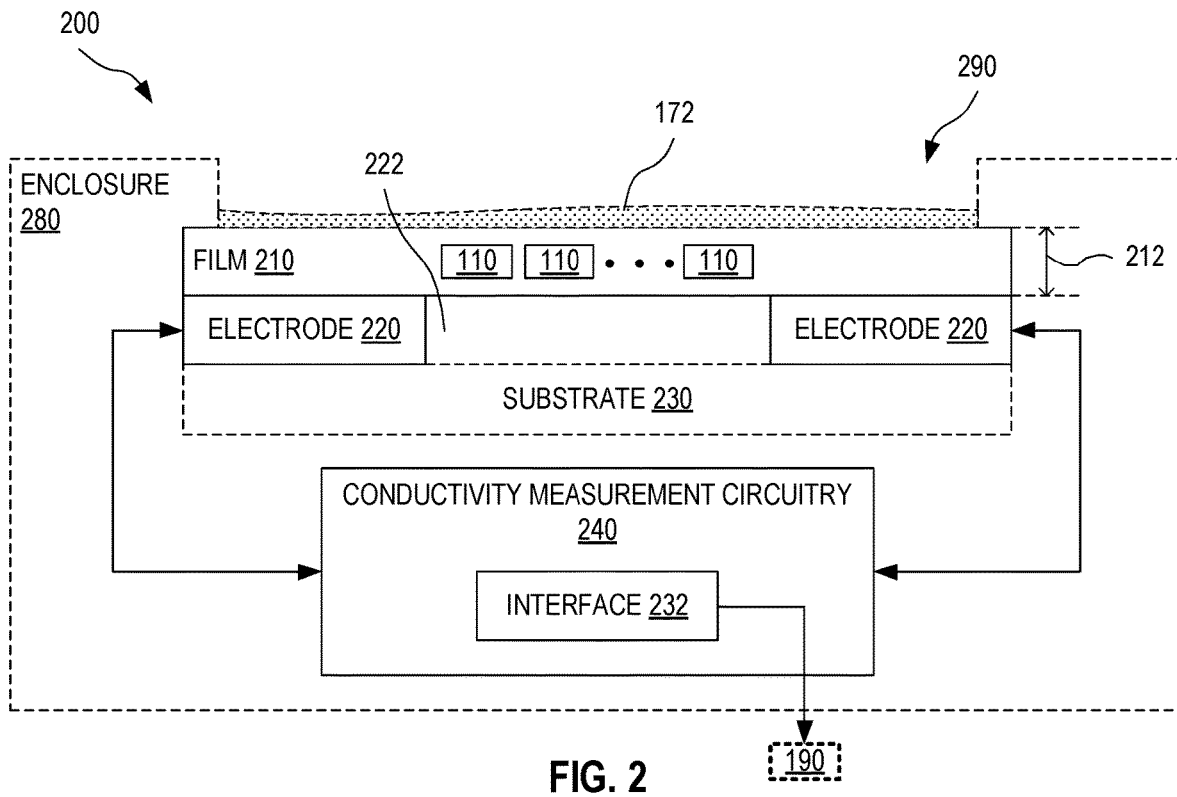
FIG. 2 is a schematic view of a device for detecting cotinine in a liquid sample, according to an embodiment.

FIG. 2 is a schematic view of one exemplary device 200 for detecting cotinine in liquid sample 172. Device 200 is an embodiment of device 100, and may implement any one of the embodiments of device 100 discussed above in reference to FIG. 1. Device 200 includes a film 210 containing MIP coated conductive nanoparticles 110. Device 200 further includes two electrodes 220 in contact with film 210, and conductivity measurement circuitry 240 communicatively coupled with each electrode 220. By virtue of MIP coated conductive nanoparticles 110, film 210 has (a) specific affinity for binding with cotinine and (b) electrical conductivity sensitive to the amount of cotinine bound thereto.

In operation, liquid sample 172 is placed in device 200 in contact with film 210 such that cotinine in liquid sample 172 may bind to MIP coated conductive nanoparticles. Conductivity measurement circuitry 240 measures the conductivity of film 210 between electrodes 220 to detect cotinine from liquid sample 172 bound to film 210. Conductivity measurement circuitry 240 includes an interface 232. Interface 232 outputs test result 190. Test result 190 includes a measurement made by conductivity measurement circuitry 240, and/or one or more parameters derived from such measurement.

Herein, measurement of conductivity may refer to measurement of actual conductivity or measurement of a parameter related to conductivity, such as resistivity, resistance, and conductance. In an embodiment, conductivity measurement circuitry 240 is configured to pass a current through film 210 between electrodes 220 to measure the resistance of film 210 between electrodes 220. In one embodiment, test result 190 includes the conductivity or resistivity of film 210. In another embodiment, test result 190 includes the conductance or resistance of film 210 between electrodes 220. In yet another embodiment, test result 190 includes another parameter derived from the conductivity, resistivity, conductance, or resistance of film 210, such as a concentration of cotinine in liquid sample 172.

In certain implementations, conductivity measurement circuitry 240 is configured to pass a direct current (DC) through film 210 between electrodes 220 to measure the DC resistance or DC conductance of film 210 between electrodes 220.

In certain embodiments, device 200 includes a substrate 230 that supports electrodes 220 and film 210. Although shown in FIG. 2 as being planar, film 210 may deviate from being planar, without departing from the scope hereof. For example, in embodiments with electrodes 220 disposed between substrate 230 and film 210, film 210 may occupy at least some of gap 222. Furthermore, film 210 need not fully cover electrodes 220. Film 210 may have thickness 212 in the range from 100 nanometers to 1 micron. In one example, thickness 212 is in the range from 400 to 600 nanometers.

In one embodiment, film 210 may be composed of MIP coated conductive nanoparticles 110. In another embodiment, film 210 includes MIP coated conductive nanoparticles 110. For example, film 210 may be mostly composed of MIP coated conductive nanoparticles 110 but also include some polymers not bound to MIP coated conductive nanoparticles 110.

Optionally, device 200 includes an enclosure 280 that houses film 210, electrodes 220, conductivity measurement circuitry 240, and substrate 230 (if included). Enclosure 280 forms a receptacle 290 configured to receive liquid sample 172 to hold liquid sample 172 in contact with film 210. The volume capacity of receptacle 290 is for example in the range from 0.5 to 5 milliliters. This volume is sufficient for device 200 to reliably detect cotinine in liquid sample 172.

Figure 3:
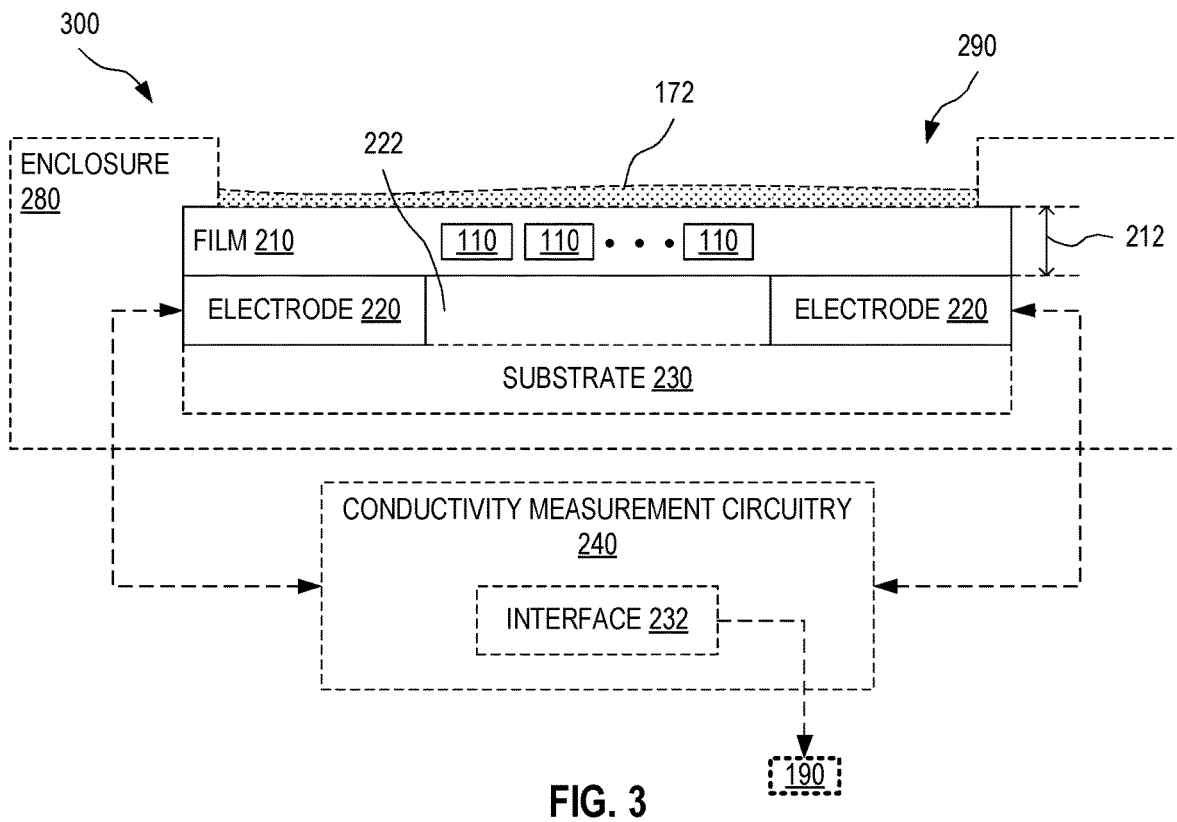
FIG. 3 is a schematic view of another device for detecting cotinine in a liquid sample, according to an embodiment.

FIG. 3 is a schematic view of another exemplary device 300 for detecting cotinine in a liquid sample 172. Device 300 is an embodiment of device 100, and may implement any one of the embodiments of device 100 discussed above in reference to FIG. 1. Device 300 is similar to device 200 except that device 300 need not include conductivity measurement circuitry 240. Embodiments of device 300 that do not include conductivity measurement circuitry 240 may be configured to cooperate with third party conductivity measurement circuitry 240 to produce test result 190. Such third party conductivity measurement circuitry 240 may be placed externally to enclosure 280.

Figure 4:
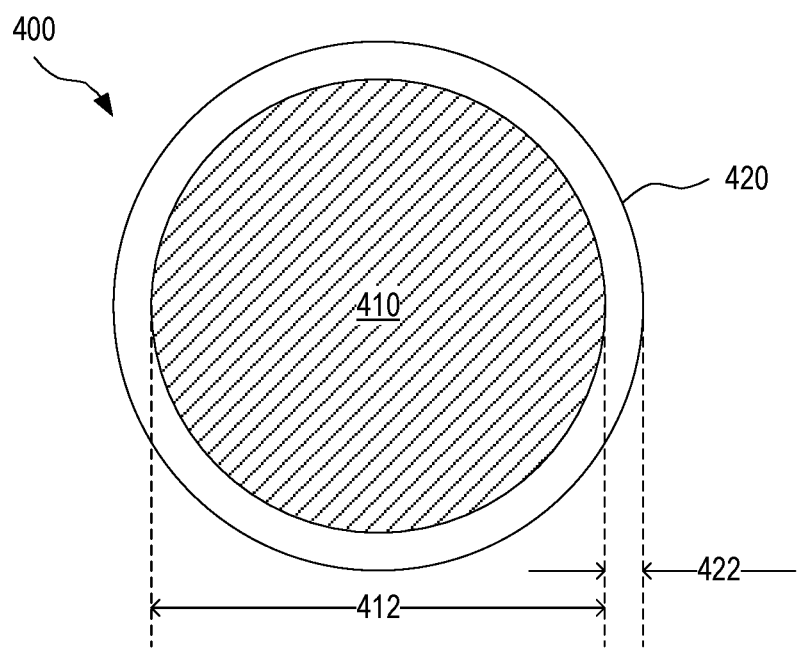
FIG. 4 illustrates a molecularly-imprinted-polymer coated conductive nanoparticle, according to an embodiment.

FIG. 4 illustrates one exemplary MIP coated conductive nanoparticle 400 which is an embodiment of MIP coated conductive nanoparticle 110 and may be implemented in film 210. MIP coated conductive nanoparticle 400 includes a conductive core 410 and a MIP shell 420 around core 410. MIP shell 420 is a coating that is composed of, or includes, molecularly imprinted polymers, imprinted with cotinine, such that MIP shell 420 has specific affinity for binding with cotinine. Conductive core 410 is electrically conductive. However, the conductivity of MIP coated conductive nanoparticle 400 is affected by MIP shell 420. The resistivity of MIP shell 420 increases with the amount of cotinine bound thereto, such that the conductivity of MIP coated conductive nanoparticle 400 decreases with the amount of cotinine bound thereto. Thus, when MIP coated conductive nanoparticles 400 are implemented in device 100, for example in film 210 of device 200 or 300, the conductivity of film 210 decreases with the amount of cotinine in liquid sample 172.

In one embodiment, conductive core 410 is a metal core essentially consisting of a metal such as gold, silver, platinum, or a combination thereof. In another embodiment, conductive core 410 includes both metal (such as gold, silver, platinum, or a combination thereof) and non-conductive material. In yet another embodiment, conductive core 410 includes a non-metallic conductive material such as graphite, optionally in combination with conductive metal and/or non-conductive material.

MIP shell 420 includes a polymer that is capable of hydrogen bonding with cotinine to facilitate affinity for binding of cotinine to MIP shell 420. In one embodiment, MIP shell 420 includes, or is substantially composed of, a homopolymer molecularly imprinted with cotinine and capable of hydrogen bonding. For example, MIP shell 420 may be substantially composed of polyvinylpyrrolidone (PVP) or poly(methyl methacrylate) (PMMA), each molecularly imprinted with cotinine. In another embodiment, MIP shell 420 includes, or is substantially composed of a copolymer molecularly imprinted with cotinine and capable of hydrogen bonding. As compared to homopolymer based embodiments of MIP shell 420, the copolymer may enhance the sensitivity of MIP shell 420 to binding of cotinine therewith. Thus, copolymer based embodiments of MIP shell 420 may exhibit increased efficiency for binding with cotinine, and hence increased sensitivity, such that devices 100 utilizing a copolymer based embodiment of MIP shell 420 may be capable of detecting lower cotinine concentrations, as compared to devices 100 utilizing a homopolymer based embodiment of MIP shell 420. In one implementation, MIP shell 420 is substantially composed of PVP-co-PMMA.

Core 410 may have diameter 412 in the range from 10 to 100 nanometers. MIP shell 420 may have thickness 422 in the range from 10 to 50 nanometers.

Figure 5:
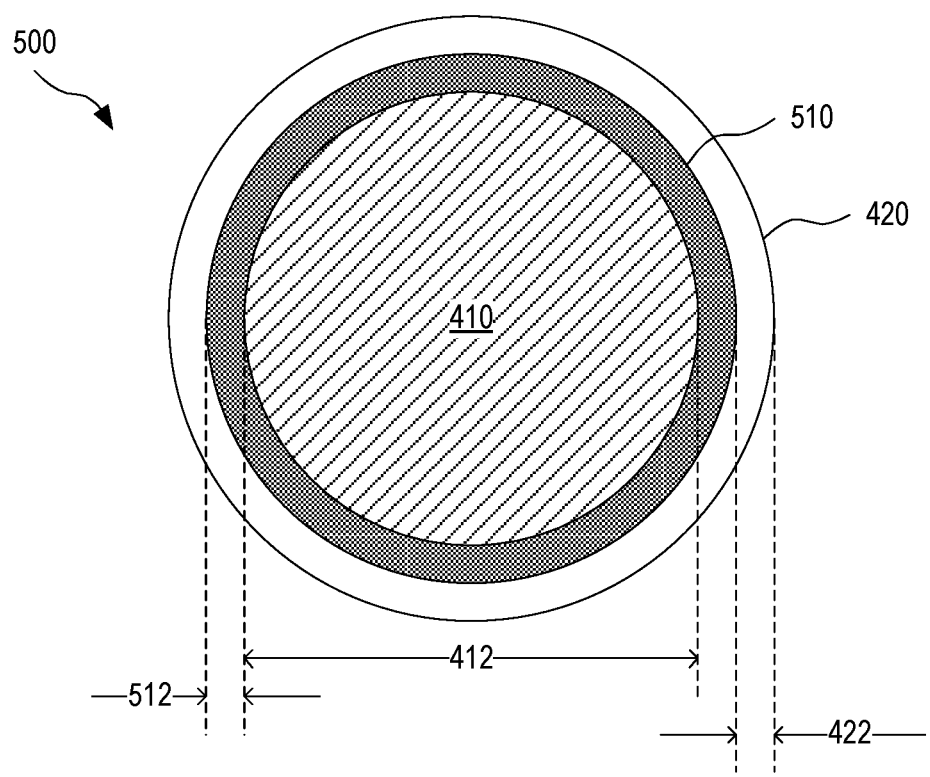
FIG. 5 illustrates a molecularly-imprinted-polymer coated conductive nanoparticle with a binding layer that aids binding of the molecularly imprinted polymer to the conductive core, according to an embodiment.

FIG. 5 illustrates one exemplary MIP coated conductive nanoparticle 500 with a binding layer that aids binding of the molecularly imprinted polymer to the conductive core. MIP coated conductive nanoparticle 500 is an embodiment of MIP coated conductive nanoparticle 110, which is similar to MIP coated conductive nanoparticle 400. MIP coated conductive nanoparticle 500 includes conductive core 410, MIP shell 420, and a binding layer 510 disposed on conductive core 410 between conductive core 410 and MIP shell 420. Binding layer 510 forms an inner shell around conductive core 410. Binding layer 510 aids the binding of the polymer of MIP shell 420 to conductive core 410.

In one embodiment, binding layer 510 is substantially composed of silicon dioxide (i.e., silica). In another embodiment, binding layer 510 is substantially composed of alumina. In yet another embodiment, binding layer 510 includes silicon dioxide and/or alumina. Binding layer 510 may have thickness 512 of about 10 nanometers, for example in the range from 3 to 30 nanometers.

Figure 6A:
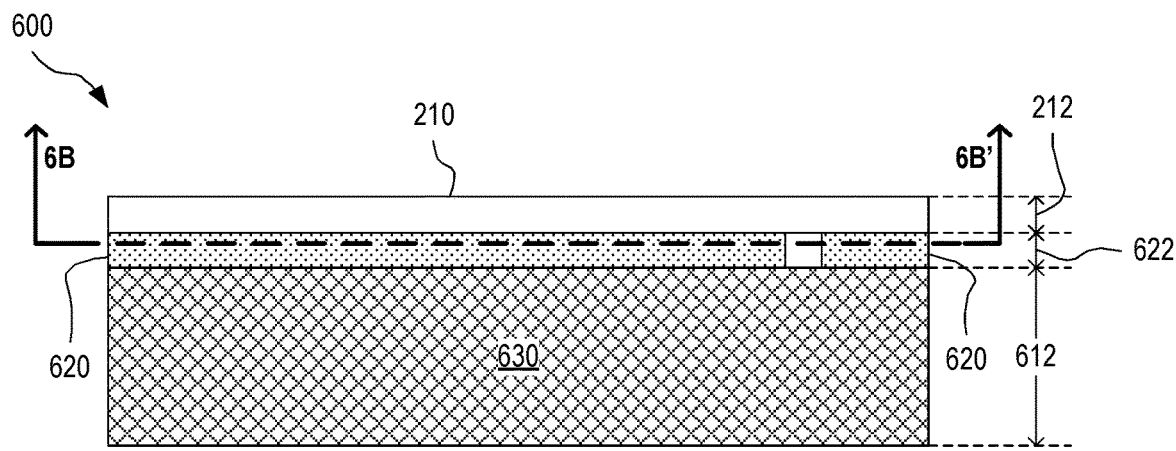
FIGS. 6A and 6B illustrate a sensing unit for detection of cotinine, which includes interdigitated electrodes, according to an embodiment.
Figure 6B:
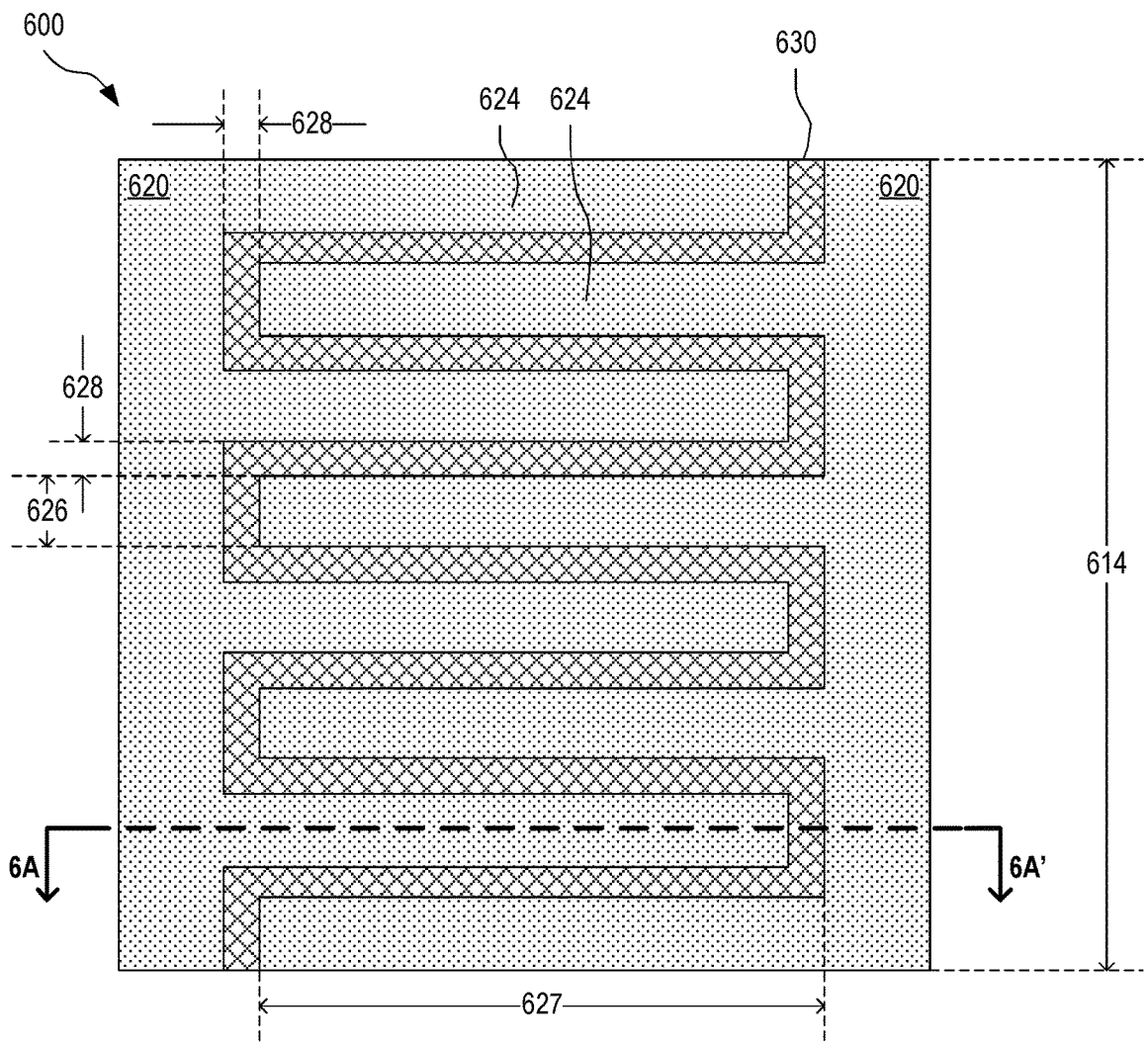

FIGS. 6A and 6B illustrate one exemplary sensing unit 600 with interdigitated electrodes. Sensing unit 600 may be implemented in device 100. Sensing unit 600 forms an embodiment of film 210, electrodes 220, and substrate 230 of devices 200 and 300. FIGS. 6A and 6B shows sensing unit 600 in orthogonal cross-sectional views. FIG. 6A is a view of a cross section taken along line 6A-6A' in FIG. 6B. FIG. 6B is a view of a cross section taken along line 6B-6B' in FIG. 6A. FIGS. 6A and 6B are best viewed together.

Sensing unit 600 includes a substrate 630, interdigitated electrodes 620, and film 210. Substrate 630 is an embodiment of substrate 230. Interdigitated electrodes 620 are an embodiment of electrodes 220. Each electrode 620 has a plurality of fingers 624. For clarity of illustration, not all fingers 624 are labeled in FIGS. 6A and 6B. Fingers 624 of one electrode 620 are interdigitated with fingers 624 of the other electrode 620. Since electrodes 620 are interdigitated, sensing unit 600 facilitates a high degree of spatial averaging over the extent of film 210, in a manner that is conceptually equivalent to making many parallel conductivity measurements for different portions of film 210. This helps ensure high accuracy of a conductivity measurement made by, for example conductivity measurement circuitry 240.

Each finger 624 has height 622, width 626, and length 627. Height 622 is for example in the range from 50 to 200 nanometers, such as approximately 100 nanometers. Width 626 is for example in the range from 10 to 100 microns, such as approximately 40 microns. Length 627 is for example in the range from 0.5 to 3 centimeters, such as approximately 2 centimeters. Adjacent fingers 624 are spaced apart from each other by a spacing 628. Spacing 628 is for example in the range from 5 to 50 microns, such as approximately 20 microns. Each electrode 620 may include between 50 and 300 fingers 624, for example approximately 150 fingers 624.

Substrate 630 is a dielectric material such as silicon dioxide. Interdigitated electrodes 620 are for example metallic. In one embodiment, interdigitated electrodes 620 are deposited on substrate 630 using photolithography. Interdigitated electrodes 620 may be chromium electrodes, optionally with a nickel overlayer between the chromium and film 210. Substrate 630 has thickness 612 sufficient to avoid breakage of sensing unit 600. Thickness 612 may be in the range from 0.75 to 1.0 millimeters.

The transverse extents 614 (only one shown in FIG. 6B) are configured to provide a contact area between liquid sample 172 and film 210 sufficiently large to (a) accommodate a sample volume sufficient for detection of cotinine at a desired sensitivity level while (b) keeping the diffusion time for cotinine in liquid sample 172 to the surface of film 210 sufficiently low to detect cotinine in liquid sample, and optionally measure its concentration, within a desired duration. In one example, the surface area of film 210 is in the range between 200 and 1000 millimeters$^2$. With a surface area of 400 millimeters$^2$, film 210 of sensing unit 600 may accommodate a 1.0 milliliter liquid sample 172 with a column height of 2.5 millimeters.

Without departing from the scope hereof, transverse extent 614 of substrate 630 may exceed transverse extent 614 of interdigitated electrodes 620 and/or transverse extent 614 of interdigitated electrodes 620 may exceed transverse extent 614 of film 210.

Figure 7:
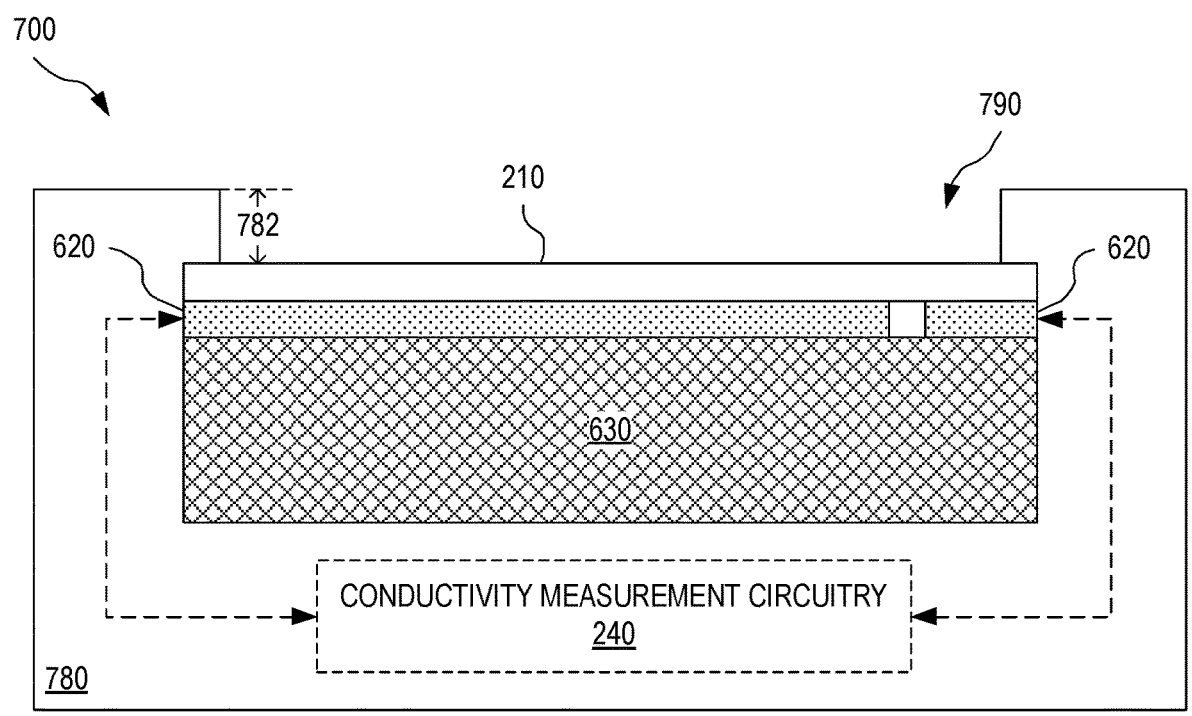
FIG. 7 illustrates a packaged sensing unit for detection of cotinine, which includes interdigitated electrodes, according to an embodiment.

FIG. 7 illustrates one exemplary packaged sensing unit 700. Sensing unit 700 is an extension of sensing unit 600, which further includes an enclosure 780. Sensing unit 700 may be implemented in device 100. Sensing unit 700 forms an embodiment of film 210, electrodes 220, substrate 230, and enclosure 280 of devices 200 and 300. Enclosure 780 contains sensing unit 600. Optionally, sensing unit 700 further includes conductivity measurement circuitry 240 communicatively with interdigitated electrodes 620 and contained within enclosure 780. Enclosure 780 is configured with an opening 790 over film 210. Opening 790 has height 782 and forms a receptacle for receiving liquid sample 172 and holding liquid sample 172 in contact with film 210. This receptacle is an embodiment of receptacle 290.

In one example, height 782 is at least 1 millimeter. In another example, height 782 is at least 2.5 millimeters. In yet another example, height 782 is at least 5 milliliters.

Figure 8:
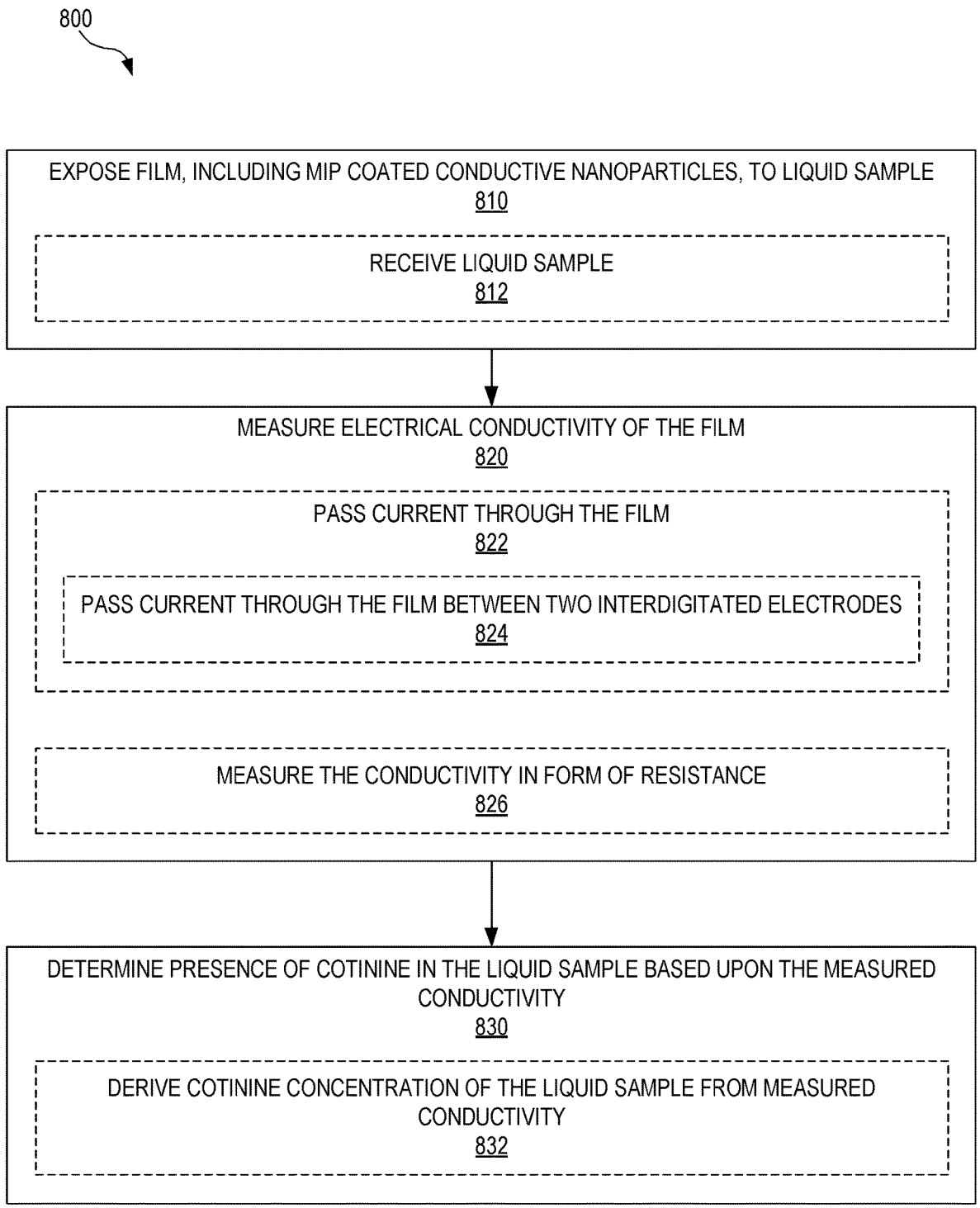
FIG. 8 illustrates a method for detecting cotinine in a liquid sample, according to an embodiment.

FIG. 8 illustrates one exemplary method 800 for detecting cotinine in liquid sample 172. Method 800 may be performed by device 100, or one of devices 200 and 300, optionally implementing either one of sensing units 600 and 700.

In a step 810, a film that includes MIP coated conductive nanoparticles 110 is exposed to liquid sample 172. Step 810 may include a step 812 of receiving liquid sample 172. In one example of step 810, liquid sample 172 is placed in receptacle 290 of device 200 or 300 and in contact with film 210.

A step 820 measures the electrical conductivity of the film of step 810. In one example of step 820, conductivity measurement circuitry 240 measures the conductivity of film 210 between electrodes 220. Step 820 may include a step 822 of passing current through the film. Step 822 is for example performed by conductivity measurement circuitry 240 via electrodes 220. In certain embodiments, step 822 includes a step 824 of passing electrical current through the film between interdigitated electrodes. In one example of step 824, conductivity measurement circuitry 240 passes current through film 210 between interdigitated electrodes 620. Optionally, step 820 implements a step 826 of measuring the conductivity of the film in the form of resistance. In one example of step 826, conductivity measurement circuitry 240 measures the resistance of film 210 between electrodes 220 or between interdigitated electrodes 620.

In a step 830, method 800 determines the presence (or absence) of cotinine in liquid sample 172 based upon the conductivity measured in step 820. In one example of step 830, conductivity measurement circuitry 240 outputs a test result 190 based upon the conductivity measured in step 820, wherein the test result 190 indicates if cotinine was or was not present (at a detectable level) in liquid sample 172. In certain embodiments, step 830 includes a step 832 of deriving the cotinine concentration in liquid sample 172 from the measured conductivity. In one example of step 830, conductivity measurement circuitry 240 derives the cotinine concentration in liquid sample 172 from the conductivity measured in step 820. In this example, conductivity measurement circuitry 240 may output the cotinine concentration as test result 190. In another example of step 830, a user derives the cotinine concentration in liquid sample 172 from test result 190 produced by device 100. The user may utilize a lookup table supplied to the user together with device 100 to convert test result 190 to a cotinine concentration.

Figure 9:
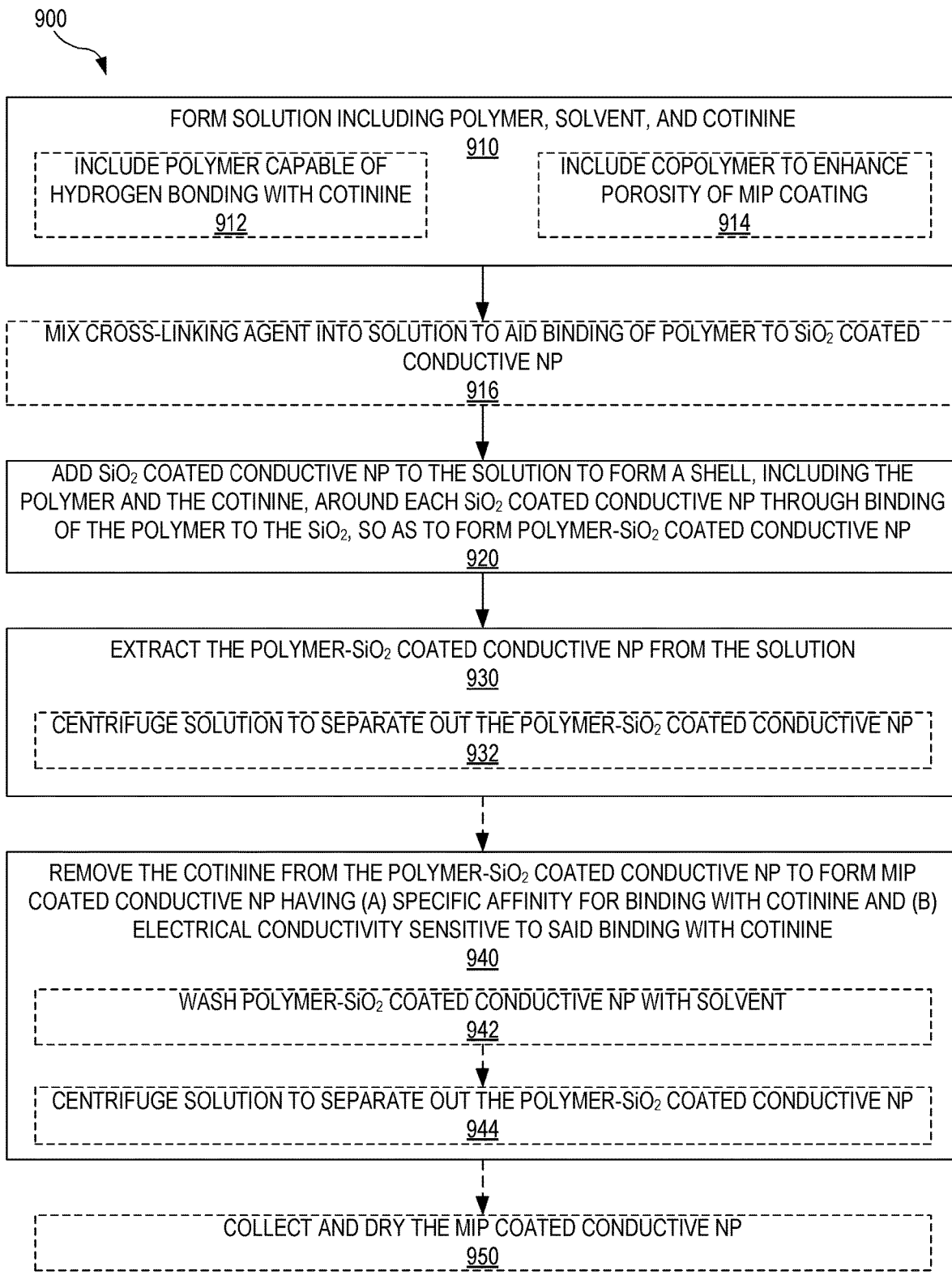
FIG. 9 illustrates a method for producing molecularly-imprinted-polymer coated conductive nanoparticles configured for cotinine detection, according to an embodiment.

FIG. 9 illustrates one exemplary method 900 for producing MIP coated conductive nanoparticles configured for cotinine detection, such as MIP coated conductive nanoparticles 110 or 500. Method 900 is for example used to manufacture device 100.

A step 910 forms a solution including polymer, a solvent, and cotinine. Step 910 dissolves the polymer and cotinine in the solvent and optionally mixes the solution for a period of time. In one example of step 910, the polymer is dissolved in dichloromethane and dimethylformamide with cotinine. In certain embodiments, step 910 implements a step 912 of including a polymer capable of hydrogen bonding with cotinine. Examples of such polymers include PVP and PMMA, and combinations thereof. Step 910 may implement a step 914 of including a copolymer to enhance the sensitivity of the MIP coating, of the MIP conductive nanoparticles produced by method 900, to binding of cotinine therewith. In one embodiment, step 910 implements both step 912 and step 914. In an example of this embodiment, PVP-co-PMMA and cotinine are dissolved in a solvent, and optionally mixed for a period of time. As discussed above in reference to FIG. 4, PVP-co-PMMA is capable of hydrogen bonding with cotinine. PVP-co-PMMA also demonstrates enhanced sensitivity to binding of cotinine therewith as compared to PVP alone or PMMA alone.

In a step 920, method 900 adds silicon dioxide coated conductive nanoparticles to the solution formed in step 910. Each silicon dioxide coated nanoparticles is, for example, core 410 with binding layer 510, wherein binding layer 510 is substantially composed of silicon dioxide. Optionally, a catalyst is added to the solution to facilitate binding of the polymer to the silicon dioxide. While in the solution, the silicon dioxide coated conductive nanoparticles are coated with the polymer and cotinine through binding of the polymer to the silicon dioxide. Step 920 thus forms a shell around each silicon dioxide coated nanoparticle. The product of step 920 is a solution that contains polymer-silicon dioxide coated conductive nanoparticles. For each polymer-silicon dioxide coated conductive nanoparticle, the polymer forms an outer shell around the silicon dioxide shell, and the polymer shell has cotinine embedded therein. The silicon dioxide-coated conductive nanoparticles are, for example, silicon dioxide-coated metal nanoparticles, wherein each metal nanoparticle includes or is composed of gold, silver, and or platinum, for example. Alternatively, the silicon dioxide-coated conductive nanoparticles are non-metallic conductive nanoparticles (such as discussed above in reference to FIG. 4) coated with silicon dioxide.

In certain embodiments, method 900 includes a step 916 that is performed between steps 910 and 920. In step 916, method 900 mixes a cross-linking agent into the solution to aid binding of the polymer to the silicon dioxide coated conductive nanoparticles in step 920. The cross-linking agent is for example tetraethyl orthosilicate (TEOS). The cross-linking agent may cooperate with the optional catalyst of step 920 to aid binding of the polymer to the silicon dioxide in step 920.

In a step 930, method 900 extracts the polymer-silicon dioxide coated conductive nanoparticles from the solution. Step 930 may implement a step 932 of centrifuging the solution to separate out the polymer-silicon dioxide coated conductive nanoparticles.

A step 940 removes the cotinine from the polymer-silicon dioxide coated conductive nanoparticles, of step 930, to form MIP coated conductive nanoparticles having (a) specific affinity for binding with cotinine and (b) electrical conductivity sensitive to the amount of cotinine bound thereto. Each MIP coated conductive nanoparticles thus formed has a conductive core surrounded by an inner silicon dioxide shell that is surrounded by an outer MIP shell, molecularly imprinted with cotinine. In one example, step 940 forms MIP coated conductive nanoparticle 500 with binding layer 510 being substantially composed of silicon dioxide.

In one embodiment, step 940 includes steps 942 and 944. In step 942, the polymer-silicon dioxide coated conductive nanoparticles extracted in step 930 are washed in a solvent to remove the cotinine from the polymer shell of each polymer-silicon dioxide coated conductive nanoparticle to form the MIP coated conductive nanoparticles. In one example, the solvent used in step 942 is an aromatic solvent such as toluene, xylene, benzene, or a combination thereof. In step 944, this solution is centrifuged to separate out the MIP coated conductive nanoparticles.

Optionally, method 900 includes a step 950 of collecting and drying the MIP coated conductive nanoparticles. In one example, step 950 dries the MIP coated conductive nanoparticles in vacuum.

In an alternative embodiment, method 900 utilizes alumina coated conductive nanoparticles instead of silicon dioxide coated conductive nanoparticles.

In one example of method 900, 0.5 grams of PVP-co-PMMA and 0.25 grams of cotinine are dissolved in 3 milliliters of dichloromethane and 2 milliliters dimethylformamide in step 910. Also as part of step 910, this solution is stirred continuously for several hours, such as at least 6 hours. Next, in step 916 of this example of method 900, 1 milliliter of TEOS is added to the solution. This addition may be performed as a dropwise addition over 5 minutes. Subsequently, in step 920 of this example of method 900, 0.01 grams of silicon dioxide coated gold nanoparticles (AuNP@$SiO_2$—NP) and 0.2 milliliters of 0.01 mole hydrochloric acid are added to the solution, and the solution is stirred for several hours, such as at least 6 hours. Hydrochloric acid functions as a catalyst for the TEOS polymerization in step 920. In this example, step 920 forms PVP-co-PMMA coated silicon dioxide coated gold nanoparticles, wherein the PVP-co-PMMA layer has cotinine embedded therein. Step 930 of this example of method 900 implements an example of step 932, wherein the solution is centrifuged at 5000 revolutions per minute for 5 minutes to separate out the PVP-co-PMMA coated silicon dioxide coated gold nanoparticles. Step 940 of this example of method 900 implements steps 942 and 944. In this example, the PVP-co-PMMA coated silicon dioxide coated gold nanoparticles are washed with toluene in step 942 to remove the cotinine, to form molecularly imprinted PVP-co-PMMA coated silicon dioxide coated gold nanoparticles. Step 944 then separates out the molecularly imprinted PVP-co-PMMA coated silicon dioxide coated gold nanoparticles from the solution by centrifugation in step 944. Each of these molecularly imprinted PVP-co-PMMA coated silicon dioxide coated gold nanoparticles are an embodiment of MIP coated conductive nanoparticle 500 with core 410 being gold, binding layer 510 being silicon dioxide, and MIP shell 420 being PVP-co-PMMA molecularly imprinted with cotinine. Optionally, the removal of cotinine is confirmed with ultraviolet-visible spectroscopy after step 942. In step 950 of this example of method 900, the molecularly imprinted PVP-co-PMMA coated silicon dioxide coated gold nanoparticles are collected and dried in vacuum.

Although not shown in FIG. 9, method 900 may include producing the silicon dioxide coated conductive nanoparticles prior to performing step 910. In one example, citrate-stabilized gold nanoparticles are produced by the method described in the literature (see, for example, Frens, G. "Controlled nucleation for regulation of particle-size in monodisperse gold suspensions", Nat.-Phys. Sci. (1973) 241, 20-22). A 0.5 millimole aqueous solution of $HAuCl_4 \cdot 3H_2O$ (Sigma-Aldrich) is boiled for 20 minutes with 1.5 millimole $Na_3C_6H_5O_7$ (Sigma-Aldrich). During this heating period, the solution color becomes wine red indicating the presence of the nanoparticles. The solution of colloidal gold is allowed to cool to room temperature. The sol-gel process (Kobayashi, et al., "Sol-gel processing of silica-coated gold nanoparticles", Langmuir (2001) 17 6375-79) may be used to synthesize the AuNP@$SiO_2$ core-shell nanoparticles. A sample of 0.1 grams of the gold nanoparticles are suspended in 20 milliliters of a 4:1 mixture of ethanol and deionized water and sonicated for 30 minutes. At the end of the sonication period, 1 milliliter of a 25% aqueous ammonia solution and 0.8 milliliters of TEOS are added and the mixture is allowed to react for 12 hours with stirring at room temperature. The resulting silicon dioxide coated gold nanoparticles may be collected by centrifugation at 5000 rpm for 10 minutes, rinsed with deionized water, and dried using vacuum.

Figure 10:
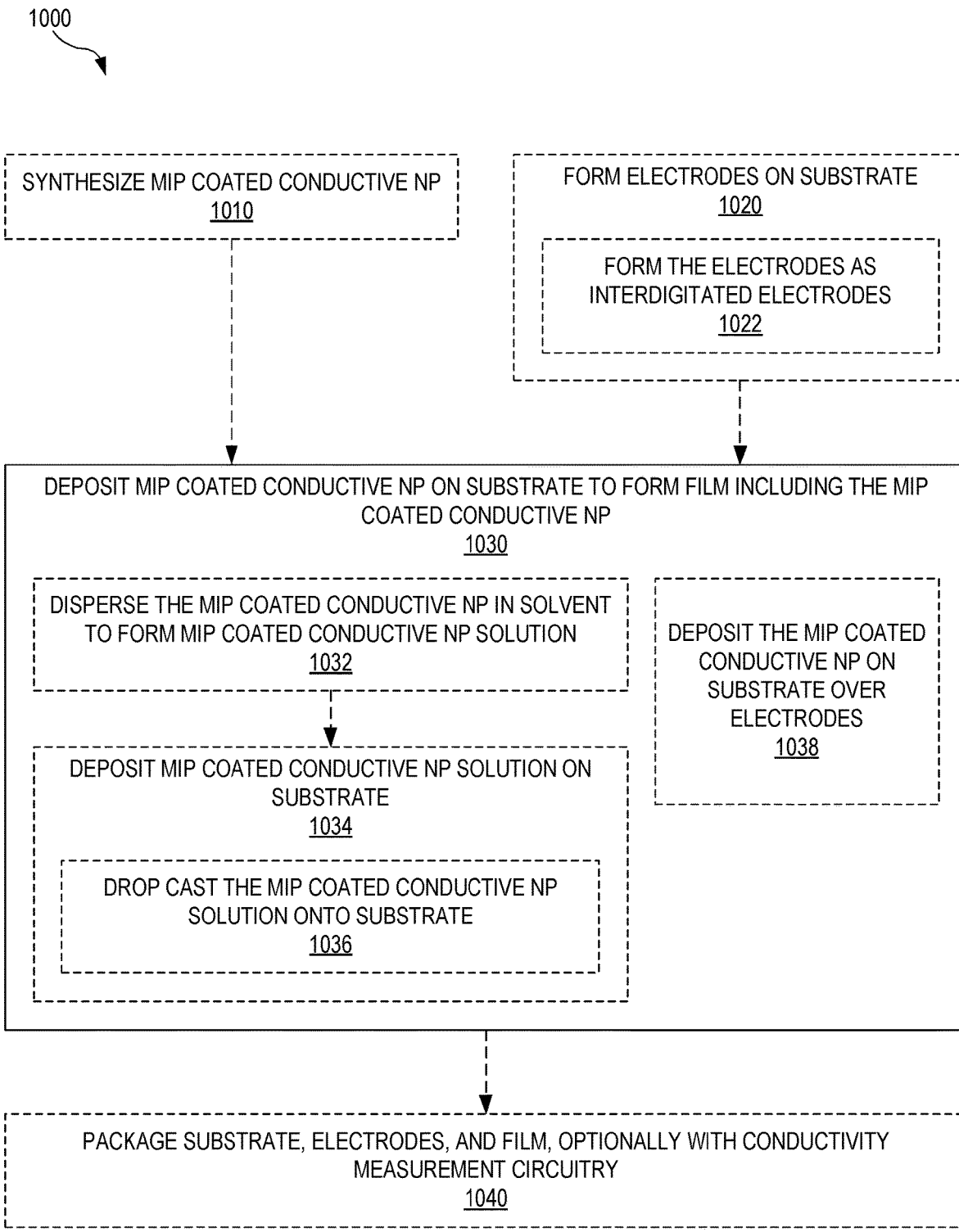
FIG. 10 illustrates a method for manufacturing a cotinine detection device, according to an embodiment.

FIG. 10 illustrates one exemplary method 1000 for manufacturing a cotinine detection device. Method 1000 may for example be used to manufacture device 100.

In a step 1030, method 1000 deposits MIP coated conductive nanoparticles on a substrate to form a film that includes the MIP coated conductive nanoparticles. In one example, step 1030 deposits MIP coated conductive nanoparticles 110 on substrate 230 to form film 210. In certain embodiments, step 1030 includes steps 1032 and 1034. Step 1032 disperses the MIP coated conductive nanoparticles in a solvent to form a MIP coated conductive nanoparticle solution. In one example of step 1032, MIP coated conductive nanoparticles 110 are dispersed in a solvent, such as dimethylformamide. For example, the molecularly imprinted PVP-co-PMMA coated silicon dioxide coated gold nanoparticles discussed above in reference to FIG. 9, and produced in the example based upon 0.5 grams of PVP-co-PMMA, may be dispersed in 5 milliliters of dimethylformamide Step 1034 deposits the solution, formed in step 1032, on the substrate. Optionally, step 1034 includes a step 1036 of drop casting the solution onto the substrate. In one example of step 1034, a 100 microliter aliquot of dispersed molecularly imprinted PVP-co-PMMA coated silicon dioxide coated gold nanoparticles (dispersed in 5 milliliters of dimethylformamide) is drop cast onto substrate 630 over interdigitated electrodes 620, wherein substrate 630 and interdigitated electrodes 620 have been pretreated with formic acid, deionized water and acetone allowed to air dry prior to drop casting.

Step 1030 produces an embodiment of at least a portion of device 100, such as (a) a sensing unit including substrate 230, electrodes 220, and film 210 forming at least a portion of device 200 or of device 300, (b) sensing unit 600, or (c) sensing unit 700.

Step 1030 may be preceded by a step 1010 of synthesizing the MIP coated conductive nanoparticles. In one embodiment, step 1010 is or includes method 900. Step 1010 produces MIP coated conductive nanoparticles 110, for example.

Step 1030 may also be preceded by a step 1020 of forming electrodes on the substrate. In one example, step 1020 forms electrodes 220 on substrate 230. In certain embodiments, step 1020 implements a step 1022 of forming the electrodes as interdigitated electrodes. In one example, step 1022 forms interdigitated electrodes 620 on substrate 630.

In embodiment of method 1000 that include step 1020, step 1030 implements a step 1038 of depositing the MIP coated conductive nanoparticles on the substrate over the electrodes. In one example of step 1038, MIP coated conductive nanoparticles 110 are deposited on substrate 230, including over electrodes 220, to form film 210, as discussed above in reference to FIG. 2. In another example of step 1038, MIP coated conductive nanoparticles 110 are deposited on substrate 630, including over interdigitated electrodes 620, to form film 210, as discussed above in reference to FIGS. 6A and 6B.

In an embodiment, method 1000 further includes a step 1040 of packaging the substrate, electrodes, and film, and optionally conductivity measurement circuitry to form a packaged device for detecting cotinine. In one example of step 1040, the sensing unit formed in step 1030 is packaged in enclosure 280, optionally together with conductivity measurement circuitry 240.

Figure 11:
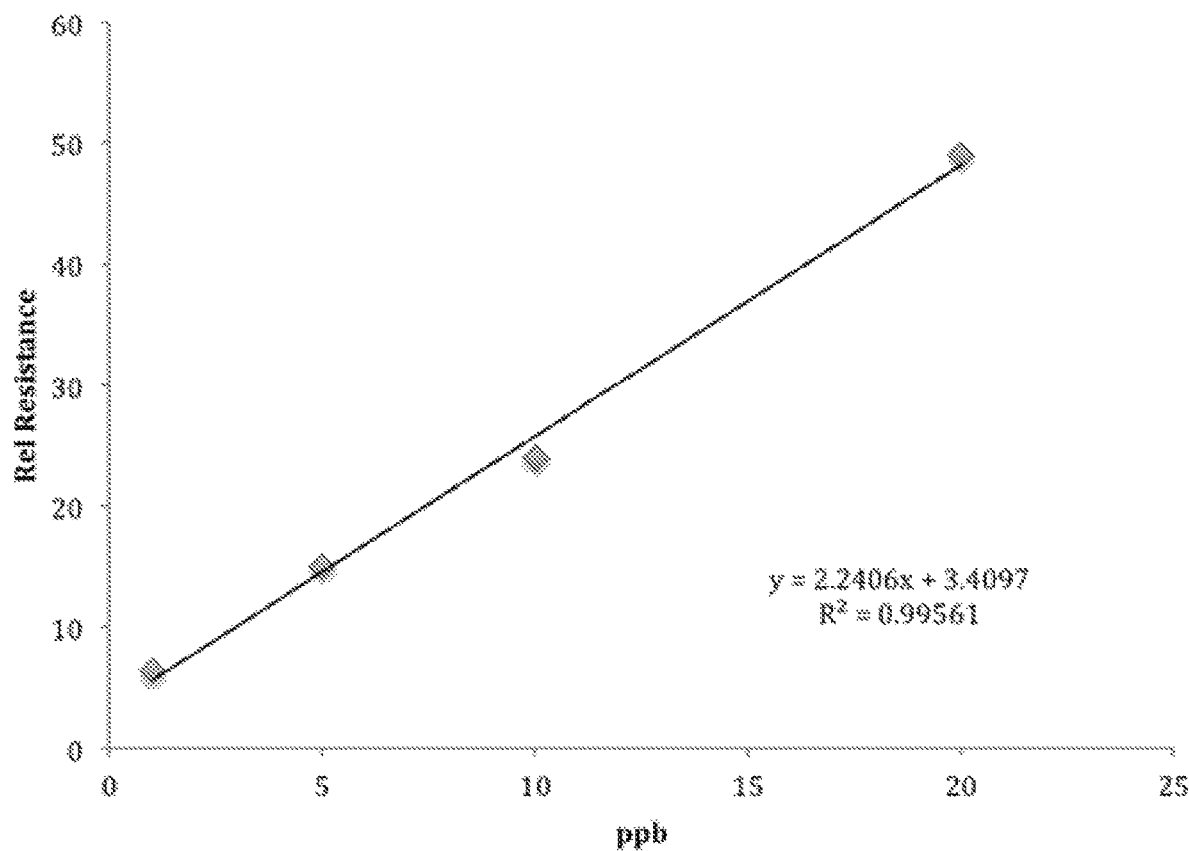
FIG. 11 shows exemplary data obtained for an embodiment of the device of FIG. 1 implementing an example of the sensing unit of FIGS. 6A and 6B with molecularly imprinted polyvinylpyrrolidone-co-poly(methyl methacrylate) coated silicon dioxide coated gold nanoparticles.

FIG. 11 shows exemplary data obtained for an embodiment of device 100 implementing an example of sensing unit 600 with molecularly imprinted PVP-co-PMMA coated silicon dioxide coated gold nanoparticles. The molecularly imprinted PVP-co-PMMA coated silicon dioxide coated gold nanoparticles are produced as discussed above in reference to FIG. 9 and incorporated in a cotinine detection device manufactured according to method 1000, as discussed above in reference to FIG. 10. The data of FIG. 11 was obtained using a multimeter (Keithley model 2000) as an embodiment of conductivity measurement circuitry 240.

The device associated with the data of FIG. 11 had interdigitated electrodes 620, and each electrode 620 had 158 fingers 624. Height 622, width 626, and spacing 628 were 100 nanometers, 40 microns, and 20 microns, respectively. Film 210 had thickness 212 of about 500 nanometers.

The multimeter measured the resistance between interdigitated electrodes 620 as a function of cotinine concentration in a liquid sample 172 deposited onto the film. FIG. 11 plots the relative resistance and demonstrates that this example of device 100 is sensitive to cotinine at concentrations at least as low as 5 parts per billion (ppb). (Herein, "relative resistance" refers to $(R_c - R_0)/R_0$, wherein $R_c$ is the resistance measured at the concentration indicated on the horizontal axis and $R_0$ is the resistance measured before exposing the device to this cotinine concentration.) This sensitivity is sufficient to detect second-hand smoking, which generally results in a cotinine concentration in urine in the range between 10 and 30 nanograms/milliliter (10 to 30 ppb). Furthermore, FIG. 11 shows that the device is capable of quantitatively and accurately distinguish different concentrations at least in the range from 5 ppb to 20 ppb. In this range, the device displays a nearly linear relationship between the measured resistance and the cotinine concentration. Additional measurements made in the range from 20 ppb to 200 ppb, not shown in FIG. 11, shows that the relative resistance quantitatively depends on the cotinine concentration also in this range.

Combinations of Features

Features described above as well as those claimed below may be combined in various ways without departing from the scope hereof. For example, it will be appreciated that aspects of one MIP coated conductive nanoparticle for cotinine detection, or associated method or device, described herein, may incorporate or swap features of another MIP coated conductive nanoparticle for cotinine detection, or associated method or device, described herein. The following examples illustrate some possible, non-limiting combinations of embodiments described above. It should be clear that many other changes and modifications may be made to the systems and methods herein without departing from the spirit and scope of this invention:

(A1) A MIP coated conductive nanoparticle for detecting cotinine may include (a) a conductive nanoparticle capable of conducting an electrical current, (b) a silicon dioxide coating formed on the conductive nanoparticle and forming a first shell around the conductive nanoparticle, and (c) an MIP coating formed on the silicon dioxide coating and forming the second shell, wherein the MIP coating includes a polymer molecularly imprinted with cotinine to provide specific affinity for binding of cotinine to the MIP coated conductive nanoparticle such that the cotinine is detectable as a change in electrical conductivity of the MIP coated conductive nanoparticle.

(A2) In the MIP coated conductive nanoparticle denoted as (A1), the conductive nanoparticle may be a metal nanoparticle.

(A3) In the MIP coated conductive nanoparticle denoted as (A2), the metal nanoparticle may include gold.

(A4) In any of the MIP coated conductive nanoparticles denoted as (A1) through (A3), the polymer may be a dielectric polymer.

(A5) In the MIP coated conductive nanoparticle denoted as (A4), the dielectric polymer may be capable of hydrogen bonding with the cotinine.

(A6) In either or both of the MIP coated conductive nanoparticles denoted as (A4) and (A5), the dielectric polymer may include a copolymer.

(A7) In the MIP coated conductive nanoparticle denoted as (A6), the copolymer may be polyvinylpyrrolidone-co-poly(methyl methacrylate).

(A8) In either or both of the MIP coated conductive nanoparticles denoted as (A6) and (A7), the copolymer may be capable of hydrogen bonding with the cotinine.

(B1) A device for detecting cotinine may include a film including a plurality of MIP coated conductive nanoparticles having specific affinity for binding with cotinine, and two electrodes in contact with the film for passing electrical current through the film to detect said binding as a change in electrical conductivity of the film.

(B2) In the device denoted as (B1), each of the MIP coated conductive nanoparticles may include (a) a conductive nanoparticle for providing electrical conductivity to the MIP coated conductive nanoparticle, and (b) an MIP coating forming an outer shell around the conductive nanoparticle, the MIP coating including a polymer molecularly imprinted with cotinine to provide specific affinity for binding of cotinine to the MIP coated conductive nanoparticle.

(B3) In the device denoted as (B2), each of the MIP coated conductive nanoparticles may further include a silicon dioxide coating disposed on the conductive nanoparticle and forming an intermediate shell around the conductive nanoparticle between the conductive nanoparticle and the outer shell, to enable formation of the MIP coating.

(B4) In either or both of the devices denoted as (B2) and (B3), the conductive nanoparticle may be a metal nanoparticle.

(B5) In the device denoted as (B4), the metal nanoparticle may include gold.

(B6) In any of the devices denoted as (B1) through (B5), the polymer may be a dielectric polymer.

(B7) In the device denoted as (B6), the dielectric polymer may be capable of hydrogen bonding with the cotinine.

(B8) In either or both of the devices denoted as (B6) and (B7), the dielectric polymer may include a copolymer.

(B9) In the device denoted as (B8), the copolymer may be polyvinylpyrrolidone-co-poly(methyl methacrylate).

(B10) In either or both of the devices denoted as (B8) and (B9), the copolymer may be capable of hydrogen bonding with the cotinine.

(B11) In any of the devices denoted as (B1) through (B10), the electrodes may be interdigitated electrodes.

(B12) In the device denoted as (B11), each of the interdigitated electrodes may have finger width in the range from 10 to 100 microns, and the spacing between the interdigitated electrodes may be in the range from 5 to 50 microns.

(B13) In any of the devices denoted as (B1) through (B12), the film may have thickness in the range from 100 nanometers to 1 micron.

(B14) Any of the devices denoted as (B1) through (B13) may further include a receptacle for receiving a liquid sample and placing the liquid sample in contact with the film to determine presence of cotinine in the liquid sample.

(B15) The device denoted as (B14) may further include an enclosure for containing the film and the interdigitated electrodes, wherein the receptacle is implemented as an opening formed in the enclosure above the film.

(B16) In either or both of the devices denoted as (B14) and (B15), the receptacle may have volume capacity in the range between 0.5 and 5 milliliters.

(B17) In any of the devices denoted as (B1) through (B16), the film and the interdigitated electrodes may be cooperatively configured to produce a linear relationship between (i) resistance measured between the interdigitated electrodes and (ii) concentration of cotinine in a liquid sample placed in contact with the film.

(B18) In any of the devices denoted as (B1) through (B17), the MIP coated conductive nanoparticles may include any one of the MIP coated conductive nanoparticles denoted as (A1) through (A8).

(C1) A method for detecting cotinine in a liquid sample may include (a) exposing a film to the liquid sample, wherein the film includes MIP coated conductive nanoparticles having specific affinity for binding with cotinine, the film having electrical conductivity sensitive to said binding, (b) measuring electrical conductivity of the film, and (c) determining presence of cotinine in the liquid sample based upon the electrical conductivity.

(C2) In the method denoted as (C1), the step of measuring may include passing electrical current through the film between two interdigitated electrodes in contact with the film.

(C3) In either or both of the methods denoted as (C1) and (C2), the step of measuring may include measuring the electrical conductivity in form of resistance of the film between the interdigitated electrodes.

(C4) In the method denoted as (C3), the step of determining may further include deriving concentration of cotinine in the liquid sample from the resistance measured in the step of measuring.

(C5) In any of the methods denoted as (C1) through (C4), the step of exposing may further include receiving the liquid sample.

(C6) In the method denoted as (C5), the step of receiving may include receiving a volume of the liquid sample in range from 0.5 to 5 milliliters.

(C7) In any of the methods denoted as (C1) through (C6), each MIP coated conductive nanoparticle may include (i) a conductive nanoparticle for providing electrical conductivity to the MIP coated conductive nanoparticle, and (ii) an MIP coating forming an outer shell around the conductive nanoparticle, the MIP coating including a polymer molecularly imprinted with cotinine to provide specific affinity for binding of cotinine to the MIP coated conductive nanoparticle.

(C8) In the method denoted as (C7), each of the MIP coated conductive nanoparticles may further include a silicon dioxide coating disposed on the conductive nanoparticle and forming an intermediate shell around the conductive nanoparticle between the conductive nanoparticle and the outer shell, to enable formation of the MIP coating.

(C9) In the method denoted as (C8), the conductive nanoparticle may be a metal nanoparticle.

(C10) In the method denoted as (C9), the metal nanoparticle may include gold.

(C11) In any of the methods denoted as (C7) through (C10), the polymer may be a dielectric polymer.

(C12) In the method denoted as (C11), in the step of exposing, the dielectric polymer may be capable of undergoing hydrogen bonding with the cotinine.

(C13) In either or both of the methods denoted as (C11) and (C12), the dielectric polymer may include a copolymer.

(C14) In the method denoted as (C13), the copolymer may be polyvinylpyrrolidone-co-poly(methyl methacrylate).

(C15) In either or both of the methods denoted as (C13) and (C14), the copolymer may be capable of hydrogen bonding with the cotinine.

(C16) In any of the methods denoted as (C1) through (C15), the MIP coated conductive nanoparticles may be include any one of the MIP coated conductive nanoparticles denoted as (A1) through (A8).

(D1) A method for manufacturing a device for detecting cotinine may include (a) making a solution including a polymer, a solvent, and cotinine, (b) adding silicon dioxide coated conductive nanoparticles to the solution to form a shell, including the polymer and the cotinine, around each of the silicon dioxide coated metal nanoparticles through binding of the polymer to the silicon dioxide, so as to form polymer-silicon dioxide coated conductive nanoparticles, (c) extracting the polymer-silicon dioxide coated conductive nanoparticles from the solution, and (d) removing the cotinine from the polymer-silicon dioxide coated conductive nanoparticles to form molecularly-imprinted-polymer (MIP) coated conductive nanoparticles having (i) specific affinity for binding with cotinine and (ii) electrical conductivity sensitive to said binding with cotinine.

(D2) The method denoted as (D1) may further include depositing the MIP coated conductive nanoparticles on a substrate to form a film including the MIP coated conductive nanoparticles.

(D3) The method denoted as (D3) may further include, before the step of depositing, forming two interdigitated electrodes on the substrate, and, in the step of depositing, depositing the MIP coated conductive nanoparticles on the substrate over the interdigitated electrodes such that the interdigitated electrodes are located between the substrate and the film.

(D4) In the method denoted as (D3), the step of depositing may include drop casting the MIP coated conductive nanoparticles on the substrate.

(D5) In either or both of the methods denoted as (D3) and (D4), the step of depositing may include dispersing the MIP coated conductive nanoparticles in a solvent to form a MIP coated conductive nanoparticle solution, and depositing the MIP coated conductive nanoparticle solution on the substrate.

(D6) Any of the methods denoted as (D1) through (D5) may further include, before the step of adding, mixing a cross linking agent into the solution to aid binding of the polymer to the silicon dioxide in the step of adding.

(D7) In the method denoted as (D6), in the step of mixing, the cross linking agent may be tetraethyl orthosilicate.

(D8) In any of the methods denoted as (D1) through (D7), the step of removing comprising washing the polymer-silicon dioxide coated conductive nanoparticles with an aromatic solvent.

(D9) In the method denoted as (D8), the aromatic solvent may be selected from the group consisting of toluene and xylene.

(D10) In any of the methods denoted as (D1) through (D9), in the step of making, the polymer may be a dielectric polymer.

(D11) In the method denoted as (D10), the polymer may include a copolymer.

(D12) In the method denoted as (D11), the copolymer may be polyvinylpyrrolidone-co-poly(methyl methacrylate).

(D13) The MIP coated conductive nanoparticle of claim 52, the copolymer being capable of hydrogen bonding with the cotinine.

(D14) In any of the methods denoted as (D1) through (D13), in the step of making, the solvent may include dichloromethane and dimethylmethacrylate.

(D15) In any of the methods denoted as (D1) through (D14), in the step of adding, each of the silicon dioxide coated conductive nanoparticles may include a metal nanoparticle.

(D16) In the method denoted as (D15), the metal nanoparticle may be a gold nanoparticle.

Changes may be made in the above compositions, devices, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present compositions, devices, and methods, which, as a matter of language, might be said to fall there between.

What is claimed is:

1. A molecularly-imprinted-polymer (MIP) coated conductive nanoparticle for detecting cotinine, comprising:
    a conductive nanoparticle capable of conducting an electrical current;
    a silicon dioxide coating formed on the conductive nanoparticle and forming a first shell around the conductive nanoparticle; and
    an MIP coating formed on the silicon dioxide coating and forming a second shell, the MIP coating comprising polyvinylpyrrolidone-co-poly(methyl methacrylate) molecularly imprinted with cotinine to provide specific affinity for binding of cotinine to the MIP coated conductive nanoparticle such that the cotinine is detectable as a change in electrical conductivity of the MIP coated conductive nanoparticle.

2. A device for detecting cotinine, comprising:
    a film including a plurality of molecularly-imprinted-polymer (MIP) coated conductive nanoparticles; and
    two electrodes in contact with the film for passing electrical current through the film to detect said binding as a change in electrical conductivity of the film;
    wherein the MIP coated conductive nanoparticles comprise:
    a conductive nanoparticle capable of conducting an electrical current;
    a silicon dioxide coating formed on the conductive nanoparticle and forming a first shell around the conductive nanoparticle; and
    an MIP coating formed on the silicon dioxide coating and forming a second shell, the MIP coating comprising polyvinylpyrrolidone-co-poly(methyl methacrylate) molecularly imprinted with cotinine to provide specific affinity for binding of cotinine to the MIP coated conductive nanoparticle such that the cotinine is detectable as a change in electrical conductivity of the MIP coated conductive nanoparticle; and
    wherein the conductive nanoparticle comprises a metal core.

3. The device of claim 2, the two electrodes being interdigitated electrodes.

4. The device of claim 3, each of the interdigitated electrodes having finger width in range from 10 to 100 microns, spacing between each of the interdigitated electrodes being in range from 5 to 50 microns.

5. The device of claim 4, the film having thickness in range from 100 nanometers to 1 micron.

6. The device of claim 2, the film having thickness in range from 100 nanometers to 1 micron.

7. The device of claim 2, further comprising a receptacle for receiving a liquid sample and placing the liquid sample in contact with the film to determine presence of cotinine in the liquid sample.

8. The device of claim 7, further comprising an enclosure for containing the film and the two electrodes, the receptacle being implemented as an opening formed in the enclosure above the film.

9. The device of claim 8, the receptacle having volume capacity in range between 0.5 and 5 milliliters.

10. The device of claim 2, the film and the interdigitated electrodes being cooperatively configured to produce a linear relationship between (a) resistance measured between the two electrodes and (b) concentration of cotinine in a liquid sample placed in contact with the film.

11. A method for detecting cotinine in a liquid sample, comprising:
    exposing a film to the liquid sample, the film including molecularly-imprinted-polymer (MIP) coated conductive nanoparticles having specific affinity for binding with cotinine, the film having electrical conductivity sensitive to said binding, each MIP coated conductive nanoparticle including:
        a conductive nanoparticle for providing electrical conductivity to the MIP coated conductive nanoparticle,
        an MIP coating forming an outer shell around the conductive nanoparticle, the MIP coating comprising polyvinylpyrrolidone-co-poly(methyl methacrylate) molecularly imprinted with cotinine to provide specific affinity for binding of cotinine to the MIP coated conductive nanoparticle, and
        a silicon dioxide coating disposed on the conductive nanoparticle and forming an intermediate shell around the conductive nanoparticle between the conductive nanoparticle and the outer shell, to enable formation of the MIP coating;
    measuring electrical conductivity of the film; and
    determining presence of cotinine in the liquid sample based upon the electrical conductivity.

12. The method of claim 11, the step of measuring comprising passing electrical current through the film between two interdigitated electrodes in contact with the film.

13. The method of claim 12, the step of measuring comprising measuring the electrical conductivity in form of resistance of the film between the interdigitated electrodes.

14. The method of claim 13, the step of determining further comprising:
    deriving concentration of cotinine in the liquid sample from the resistance measured in the step of measuring.

15. The method of claim 11, the step of exposing further comprising:
    receiving the liquid sample.

16. The method of claim 15, the step of receiving comprising receiving a volume of the liquid sample in range from 0.5 to 5 milliliters.

\* \* \* \* \*